(12) United States Patent
Wang et al.

(10) Patent No.: US 11,291,985 B2
(45) Date of Patent: Apr. 5, 2022

(54) PREPARATION METHOD FOR PROPYLENE EPOXIDATION CATALYST, AND APPLICATION THEREOF

(71) Applicant: Wanhua Chemical Group Co., Ltd., Shandong (CN)

(72) Inventors: Lei Wang, Shandong (CN); Tongji Wang, Shandong (CN); Fei Ye, Shandong (CN); Lichao Yang, Shandong (CN); Guangquan Yi, Shandong (CN); Jiaoying Cui, Shandong (CN); Naibo Chu, Shandong (CN); Yuan Li, Shandong (CN); Weiqi Hua, Shandong (CN)

(73) Assignee: Wanhua Chemical Group Co., Ltd.

( * ) Notice: Subject to any disclaimer, the term of this patent is extended or adjusted under 35 U.S.C. 154(b) by 135 days.

(21) Appl. No.: 16/646,828

(22) PCT Filed: Jun. 14, 2018

(86) PCT No.: PCT/CN2018/091243
§ 371 (c)(1),
(2) Date: Mar. 12, 2020

(87) PCT Pub. No.: WO2019/080514
PCT Pub. Date: May 2, 2019

(65) Prior Publication Data
US 2020/0269228 A1 Aug. 27, 2020

(30) Foreign Application Priority Data

Oct. 27, 2017 (CN) .......................... 201711024586.5

(51) Int. Cl.
*B01J 37/00* (2006.01)
*B01J 6/00* (2006.01)
(Continued)

(52) U.S. Cl.
CPC ........... *B01J 37/0054* (2013.01); *B01J 6/001* (2013.01); *B01J 21/08* (2013.01); *B01J 37/08* (2013.01);
(Continued)

(58) Field of Classification Search
CPC . B01J 6/001; B01J 21/08; B01J 23/002; B01J 23/36; B01J 35/1019; B01J 35/1042;
(Continued)

(56) References Cited

U.S. PATENT DOCUMENTS 3,829,392 A 8/1974 Wulff
4,859,785 A 8/1989 Bellussi et al.
(Continued)

FOREIGN PATENT DOCUMENTS

CN 1250775 A 4/2000
CN 1720100 A 1/2006
(Continued)

OTHER PUBLICATIONS

Chinese Search Report for Application No. 201711024586.5 dated Apr. 2, 2019, 4 pages.
(Continued)

*Primary Examiner* — Brian A McCaig
(74) *Attorney, Agent, or Firm* — Lerner, David, Littenberg, Krumholz & Mentlik, LLP (57) ABSTRACT

A preparation method for a propylene epoxidation catalyst: pre-hydrolyzing a silicon source, adding a titanium source and reacting to form a sol, atomizing the sol and then spraying it into liquid ammonia for molding, implementing pore broadening, and performing drying, calcination, and silanization treatment to obtain a Ti—SiO$_2$ composite oxide catalyst. The present catalyst can be used in the chemical process of preparing propylene oxide by epoxidation of
(Continued)

propylene, the average propylene oxide selectivity being up to 97.5%, having prospects for industrial application.

22 Claims, 3 Drawing Sheets

(51) Int. Cl.
   *B01J 21/08* (2006.01)
   *B01J 37/08* (2006.01)
   *C07D 301/14* (2006.01)
   *B01J 35/10* (2006.01)
   *C07D 303/04* (2006.01)

(52) U.S. Cl.
   CPC ......... *C07D 301/14* (2013.01); *B01J 35/1019* (2013.01); *B01J 35/1042* (2013.01); *B01J 35/1047* (2013.01); *B01J 35/1061* (2013.01); *C07D 303/04* (2013.01)

(58) Field of Classification Search
   CPC .................. B01J 35/1047; B01J 35/1061; B01J 37/0054; B01J 37/08; B01J 2523/00; C07D 301/14; C07D 303/04; Y02P 20/52
   See application file for complete search history.

(56) References Cited

U.S. PATENT DOCUMENTS

| | | | |
|---|---|---|---|
| 5,744,619 | A | 4/1998 | Nemeth et al. |
| 6,211,388 | B1 | 4/2001 | Tsuji et al. |
| 8,349,765 | B2 | 1/2013 | Pak et al. |
| 2003/0134741 | A1 | 7/2003 | Weisbeck et al. |
| 2003/0148885 | A1 | 8/2003 | Weisbeck et al. |
| 2003/0166951 | A1 | 9/2003 | Blankenstein et al. |
| 2005/0014960 | A1 | 1/2005 | Buijink et al. |
| 2005/0054865 | A1 | 3/2005 | Muller et al. |
| 2016/0297781 | A1 | 10/2016 | Zakzeski |
| 2020/0147599 | A1 | 5/2020 | Wang et al. |

FOREIGN PATENT DOCUMENTS

| | | |
|---|---|---|
| CN | 1894030 A | 1/2007 |
| CN | 101353169 A | 1/2009 |
| CN | 102441429 A | 5/2012 |
| CN | 102989503 A | 3/2013 |
| CN | 103464197 A | 12/2013 |
| CN | 104307514 A | 1/2015 |
| CN | 105032482 A | 11/2015 |
| CN | 105776244 A | 7/2016 |
| CN | 107224993 A | 10/2017 |
| CN | 107715868 A | 2/2018 |
| CN | 107930610 A | 4/2018 |
| WO | 03059506 A1 | 7/2003 |
| WO | 2004050241 A1 | 6/2004 |
| WO | 2010077264 A1 | 7/2010 |

OTHER PUBLICATIONS

Guo, et al., "Crystallization mechanism and catalytic performance of TS-1 synthesized by an aerosol-assisted method," CrystEngComm, 2017, pp. 2695-2701, vol. 19, No. 19, English Translation of Abstract Included Only.

Mao Weibo, "The characters and catalysis activities of micro-TS-1 modified by several kind of Alkali," Modification, characterization and catalytic properties of micron TS-1, Dalian University of Technology Master's degree thesis, pp. 1-59, Applying for a degree: Master's degree Major: Catalytic Chemistry and Engineering Mentor: Guo News 20070601, English abstract included.

Thangaraj, et al., "An improved method for TS-1 synthesis: 29Si NMR studies," Journal of the Chemical Society, Chemical Communications. Jan. 21, 1992, pp. 123-124, vol. 2, English Translation of Abstract Included Only.

Yuhai, et al., "Advances in the study of perforation of silicone in catalyst carrier," Mar. 2006, pp. 18-27, Phase 1, Gansu Chemical, China Petroleum Lanzhou Petrochemical Corporation Petrochemical Research Institute, English abstract not available.

Zhenzhen, et al., "Study of Preparation of Epoxide Olefin by Catalysts," A Thesis Submitted to the University of Jinan in Partial Fulfillment of the Requirements for the Degree of Master of Engineering Science, May 23, 2016, University of Jinan, Jinan, Shandong, P.R. China, English abstract included.

International Search Report from Application No. PCT/CN2018/091243 dated Aug. 21, 2018, 2 pages.

Extended European Search Report including Written Opinion for EP18871242.6 dated Jul. 21, 2021; 8 pages.

PREPARATION METHOD FOR PROPYLENE EPOXIDATION CATALYST, AND APPLICATION THEREOF

CROSS REFERENCE TO RELATED APPLICATIONS

The present application is a national phase entry under 35 U.S.C. § 371 of International Application No. PCT/CN2018/091243, filed Jun. 14, 2018, which claims priority from Chinese Patent Application No. 201711024586.5 filed Oct. 27, 2017, all of which are hereby incorporated herein by reference.

TECHNICAL FIELD

The present invention relates to a preparation method for a propylene epoxidation catalyst, specifically relates to a preparation method for a Ti—$SiO_2$ composite oxide catalyst and its use as a catalyst for propylene epoxidation to prepare propylene oxide.

BACKGROUND

The ethylbenzene co-oxidation process (PO/SM) with ethylbenzene hydroperoxide (EBHP) as the oxidant and the CHP process with cumyl hydroperoxide (CHP) as the oxidant are two important processes for producing propylene oxide; the two processes overcome the shortcomings of severe corrosion and large amount of sewage in the chlorohydrin process, and have the advantages of low product cost and less environmental pollution.

The catalyst used in the epoxidation step of the heterogeneous PO/SM process is a Ti—$SiO_2$ composite oxide. The preparation methods disclosed in published US patent applications U.S. Pat. No. 3,829,392, US2003166951 and published Chinese patent applications CN1894030, CN1720100 are as follows: carrying out a drying treatment to the silica gel carrier, using $N_2$ or other inert gas to bring the titanium halide vapor into the reaction tube to chemically react with the silica gel (this step is called chemical vapor deposition), calcinating at high temperature, and finally carrying out steps such as water washing to prepare a catalyst. Titanium active species have poor dispersibility on the surface of $SiO_2$, and free $TiO_2$ is easily formed, resulting in ineffective decomposition of the oxidant and reducing the selectivity to PO.

The catalyst used in the CHP process is also a Ti—$SiO_2$ composite oxide. The preparation method disclosed in published US patent applications U.S. Pat. Nos. 6,211,388, 5,744,619 and published Chinese patent application CN1250775 is a sol-gel method: dissolving a silicon source and a titanium source respectively in alcohol solvents, adding a quaternary ammonium ion (such as cetyl ammonium bromide) as a template agent, and forming a gel by hydrolysis, polymerization, and aging, followed by high-temperature calcination and silanization treatment to obtain a catalyst. Compared with the vapor deposition method, the sol-gel method can make different components miscible with each other at molecular level, and can obtain titanium active centers with nano-phase regions and even molecular dispersion. However, the chief disadvantage of the sol-gel method is that an expensive quaternary ammonium salt needs to be added as a template agent during the preparation process. Generally, the template agent must also be removed by high-temperature calcination, and the template agent cannot be recovered, resulting in higher catalyst costs.

SUMMARY

The purpose of the present invention is to provide a preparation method for a propylene epoxidation catalyst. The advantages of using the method to prepare the catalyst include:

facilitating the dispersion of Ti active species on the surface of $SiO_2$, high selectivity to PO, and low manufacturing cost.

The present invention also provides a catalyst (or refer to a Ti—$SiO_2$ composite oxide catalyst) prepared by the method, which can be used as a catalyst for the epoxidation of propylene to produce propylene oxide (PO), and has high activity and high selectivity to propylene oxide.

In order to achieve the above-mentioned object, the technical solutions adopted by the present invention are as follows:

The propylene epoxidation catalyst according to the present invention is prepared by a sol method, wherein the catalyst is obtained by molding in liquid ammonia, pore broadening, drying, calcination and silanization treatment; there is no need to use a template agent in the present invention, so the catalyst production cost is reduced. In a preferred solution, Re and Zn are used to modify the catalyst, which is obtained by molding in liquid ammonia, pore broadening, drying, calcination at high temperature and silanization treatment; there is no need to use a template agent in the present invention, the molding is carried out in liquid ammonia, more preferably the pore broadening is carried out in liquid ammonia, the catalyst production cost is greatly reduced; by using Re and Zn to modify the catalyst, the synergistic effect of Re, Zn, and Ti can improve the activity of the catalyst and the selectivity to propylene oxide.

Specifically, a preparation method for a propylene epoxidation catalyst, which comprises the following steps:

(1) pre-hydrolysis of silicon source: dissolving a silicon ester in a lower alcohol, adding a hydrolysis catalyst and water to react to obtain liquid A; in a specific embodiment, the water is preferably added dropwise in this step, and the water can be specifically deionized water;

(2) sol formation: dissolving a titanium ester in a lower alcohol and adding the system to liquid A; adding water to react to obtain a sol, or adding a mixed aqueous solution of $NH_4ReO_4$ and a zinc salt to react to obtain a sol; in a specific embodiment, after the titanium ester is dissolved in the lower alcohol in this step, the system can be added dropwise to the liquid A, the water or the mixed aqueous solution of $NH_4ReO_4$ and a zinc salt in this step can also be added dropwise;

(3) atomizing the sol obtained in step (2) and spraying it into liquid ammonia to mold to obtain a catalyst precursor; the atomization can be specifically carried out by an atomizer;

(4) carrying out a pore broadening treatment to the catalyst precursor obtained in step (3);

(5) drying and calcining the pore broadened catalyst precursor in step (4);

(6) carrying out a silanization treatment to the product obtained in step (5) to obtain a Ti—$SiO_2$ composite oxide catalyst.

In the present invention, the silicon ester in step (1) can be tetraethyl orthosilicate, tetramethyl orthosilicate, tetrapropyl orthosilicate, tetrabutyl orthosilicate or a mixture thereof; the lower alcohol can be a C1-C3 alcohol, which is mainly used as a solvent, there is no obvious difference between using different alcohols, for example, the alcohol can be one or more of methanol, ethanol, n-propanol, and isopropanol, preferably isopropanol; the concentration of silicon ester in lower alcohol is preferably 20-30 wt %; the hydrolysis catalyst is preferably formic acid, acetic acid or a mixture thereof, and the catalyst is added in an amount that is preferably 0.8-1.5 wt % of the silicon ester; the amount of water added in step (1) is preferably the amount of water theoretically required to hydrolyze 30-80 wt % of the silicon ester. The reaction temperature in step (1) is preferably 40-70° C., and the reaction time is preferably 1-3 h. In the preparation method of the present invention, pre-hydrolysis of the silicon ester is carried out firstly. This step is one of the key steps, as the hydrolysis rate of the titanium ester is fast and the hydrolysis rate of the silicon ester is slow, the hydrolysis rates of the two do not match. The inventors found that if the silicon ester is not pre-hydrolyzed, uneven distribution of Ti active component will be caused, even free $TiO_2$ will be formed, and free $TiO_2$ will cause the self-decomposition reaction of peroxides and the selectivity of the catalyst is reduced; moreover, the inventors found in experiments that a precipitate not a gel will be formed if the hydrolysis catalyst is not added and the silicon source is not pre-hydrolyzed.

In the present invention, the titanium ester used in the step (2) can be one or more of tetramethyl titanate, tetraethyl titanate, tetrapropyl titanate, tetraisopropyl titanate, tetrabutyl titanate and tetraisobutyl titanate. The amount of Ti in the used titanium ester is preferably 2-5% of the weight of $SiO_2$ from the theoretically complete hydrolysis of the raw material silicon ester in step (1) (i.e., based on the weight of $SiO_2$ corresponding to the $SiO_2$ from theoretically complete hydrolysis of the raw material silicon ester in step (1)), the concentration of the titanium ester in the lower alcohol is preferably 30-50 wt %; using the preferred amount and concentration of the titanium ester to prepare the catalyst can improve the catalyst activity and avoid the formation of free titanium dioxide to a greater extent. Preferably, the reaction time in step (2) is 1 h-4 h.

In the present invention, after the titanium ester in step (2) is completely added to the liquid A from step (1), one embodiment is to add water to react to obtain a sol; and a more preferred embodiment is to add the mixed aqueous solution of $NH_4ReO_4$ and a zinc salt instead of water to react to form a sol. In the embodiment of adding water for reaction in step (2), the amount of water used is the amount required for the theoretical complete hydrolysis of the unhydrolyzed silicon ester in step (1) and the titanium ester in step (2). In the preferred embodiment, in step (2), the concentration of the mixed aqueous solution of $NH_4ReO_4$ and the zinc salt is not particularly required. The molar ratio of Re in the used $NH_4ReO_4$ to Ti in the used titanium ester is preferably 0.01-0.05:1. The molar ratio of Zn in the used zinc salt to Ti in the used titanium ester is 0.05-0.15:1. Using a preferred ratio of $NH_4ReO_4$ to the zinc salt, a better synergistic effect can be produced by the two. Any kind of zinc salt can be used as long as it is soluble in water, for example, the zinc salt can be, but is not limited to, $ZnCl_2$, $Zn(NO_3)_2$ or a mixture thereof. In some specific embodiments, the amount of water used in the mixed aqueous solution of $NH_4ReO_4$ and a zinc salt is the amount of water required for the complete hydrolysis of the unhydrolyzed silicon ester in step (1) and the titanium ester in step (2), wherein the amount of water required for the unhydrolyzed silicon ester in step (1) can be obtained as follows: an amount of water for the complete hydrolysis of the silicon ester is calculated based on the total amount of silicon ester, and then minus the amount of water added in the step (1) for pre-hydrolyzing the silicon ester. It was found through experiments that the synergistic effect of Re and Ti (in the catalyst, the existence form of Ti is mainly T=O tetrahedron or called the tetracoordinated skeletal Ti) improves the selectivity to PO of the catalyst by adding a certain amount of Re (Re exists in the form of oxide $Re_2O_7$ in the catalyst) to modify the catalyst; by adding a certain amount of Zn (Zn exists in the form of oxide ZnO in the catalyst) to modify the catalyst, as ZnO is alkaline, it can neutralize the acidity of free $TiO_2$ formed during the preparation of the catalyst, reduce the decomposition of peroxides, and improves the selectivity to PO.

In the present invention, an atomizer such as a centrifugal atomizer is used for atomization in the step (3). In some preferred embodiments, the average particle size of the atomized sol is adjusted to 100-850 μm, preferably 400-580 μm by adjusting the nozzle size and the rotation speed. The advantages of using an atomizer to spray sol into liquid ammonia for molding are as follows: particles similar to spherical particles are directly obtained, so that a unit volume of the reactor can be filled with more catalyst; the strength of the molded particles is high, the average strength thereof reaches 23-26N/particle; compared with the molding process in oil, the step of removing oil from the molded catalyst precursor is not comprised, the process of the present invention is simpler.

In the present invention, it is preferable to use liquid ammonia as the pore broadening agent in the step (4) for the pore broadening treatment; the conditions for the pore broadening process preferably are as follows: the pore broadening agent is liquid ammonia, the temperature for pore broadening is 60-140° C., the time for pore broadening is 3-15 h. The purpose of pore broadening in the present invention is to make the catalyst form a certain pore structure, so as to expose more active Ti species, and to facilitate the contact of the reactants to the active center. In some preferred embodiments of the present invention, the specific surface area of the pore broadened catalyst is 180-300 m$^2$/g, the pore volume is 0.9-1.1 ml/g, and the average pore diameter is 8.5-13 nm. In the present invention, liquid ammonia is used as the pore broadening agent instead of ammonia water or an ammonium salt solution because the water in the ammonia water or ammonium salt solution will cause the already formed skeletal Ti species to become free $TiO_2$, which will reduce the selectivity of the catalyst to PO.

In the present invention, the drying temperature in the step (5) is 80-120° C., and the drying time is preferably 2-5 h; calcination is carried out in air or any inert atmosphere, the heating rate is not strictly limited, and a common heating rate of 1-3° C./min can be used, the calcination temperature is 450-600° C., the calcination time is 2-5 h.

In the present invention, the silanization reagent in the step (6) is hexamethyldisilazane, and the amount of the reagent used is 5-15 wt % based on the weight of the $SiO_2$ from the theoretically completely hydrolyzed silicon ester (i.e., based on the weight of $SiO_2$ corresponding to the $SiO_2$ from complete hydrolysis of the raw silicon ester in step (1)). The temperature of the hexamethyldisilazane used for the silanization treatment is preferably 126-150° C.; in some embodiments, the silanization treatment is carried out in a reaction tube, and the flow rate of $N_2$ in the reaction tube is 0.5-1 cm/s, the silanization temperature is 200-300° C., the silanization time is 60-180 min; $N_2$ is used to bring the silanization reagent vapor into the reaction tube, the chemical reaction occurred is as follows:

The purpose of the silanization treatment is to improve the hydrophobicity of the catalyst surface, to reduce the decomposition ability of the catalyst to peroxides, and to improve the selectivity of the catalyst to PO.

The catalyst obtained by the preparation method of the present invention is particularly suitable as a catalyst for the epoxidation of propylene to produce propylene oxide (PO). When it is used to catalyze the epoxidation of propylene to produce propylene oxide (PO), the conditions of the reaction process can be: the molar ratio of propylene to CHP (cumyl hydroperoxide) is 5-7:1, the mass space velocity is 2-3.5 $hr^{-1}$; the initial reaction temperature is 50-60° C., and the reaction temperature is gradually increased according to the CHP conversion rate (CHP conversion rate is guaranteed to be >99%).

With the technical solution of the present invention, the technical effects that can be obtained are as follows:

(1) The preparation method of the present invention does not need to use any templating agent, and can still achieve the technical effect that can be achieved by the catalysts prepared by using templating agents in the prior art, so the cost of the catalyst is reduced;

(2) In a preferred embodiment, the catalyst is modified by adding $NH_4ReO_4$, the auxiliary agent Re cooperates with the Ti active center, the catalyst activity and selectivity to propylene oxide are improved;

(3) In a preferred embodiment, the catalyst is modified by adding Zn, ZnO is alkaline, which can neutralize the acidity of the free $TiO_2$ formed during the preparation of the catalyst, reduce the decomposition of peroxide oxidants and improve the selectivity to PO; the average selectivity of the catalyst to PO is up to 97.5%, which reduces the consumption of propylene per unit for PO products;

(4) Spherical particles or particles that are similar to spherical particles are directly obtained by spraying the atomized sol into liquid ammonia for molding, without the time-consuming aging step of the common sol-gel method, thereby improving production efficiency;

(5) In the preparation process of the catalyst, the sol is sprayed into liquid ammonia for molding, the strength of the particles after molding is high, and the average strength reaches 23-26N/particle; compared with the molding process in oil, the step of removing oil from the molded catalyst precursor is not comprised, the process of the present invention is simpler.

EMBODIMENT

In order to better understand the present invention, the content of the present invention is further clarified below with reference to the examples, but the content of the present invention is not limited to the following examples.

The method for measuring the specific surface area and the pore structure in the examples of the present invention is the BET method ($N_2$ physical adsorption method), the model number of the instrument is ASP2020, produced by Micromeritics Instruments Corporation, USA.

The strength tester in the examples of the present invention is KC-3 digital display particle strength tester, produced by Analytical Instrument Factory of Jiangyan.

In the examples of the present invention, the content of PO in the reaction liquid and the exhaust gas absorption liquid was analyzed by gas chromatography, and the conversion rate of CHP was analyzed by iodimetry. The conditions of chromatography are shown in Table 1.

TABLE 1

Conditions for chromatographic operation

| | |
|---|---|
| Chromatographic column | Agilent 19091N-133 (30 m * 250 μm * 0.25 μm) |
| Flow rate of $H_2$ | 35 mL/min |
| Flow rate of air | 350 mL/min |
| Flow rate of makeup gas ($N_2$) | 25 mL/min |
| Heater | 270° C. |
| Column box | 250° C. |
| Heating procedure | Initial temperature: 50° C. Heating program: 50° C.-100° C. 15° C./min maintaining for 0 min 100° C.-250° C. 20° C./min maintaining for 2 min |
| Split ratio of injection port | 30:1 |
| Temperature of FID detector | 270° C. |

The content of PO was determined by internal standard method. The liquid phase concentration was determined using DMF as the solvent and DT (dioxane) as the internal standard substance. The internal standard curve of PO and DT was determined to be y=0.6985x-0.0046, $R^2$=0.999; the concentration of PO in gas phase absorption liquid was determined using toluene as the internal standard substance, the internal standard curve of PO and toluene was determined to be y=2.161x+0.0002, $R^2$=0.999.

Concentration of PO in liquid phase=(0.6985×($A_{PO}$/$A_{DT}$)−0.0046)×0.01×dilution ratio;

Content of PO in liquid phase=concentration of PO in liquid phase×weight of sample in liquid phase;

Concentration of PO in gas phase=(2.162×($A_{PO}$/$A_{toluene}$)+0.0002)×weight of toluene;

Content of PO in gas phase=concentration of PO in gas phase×total amount of absorption liquid/ amount of sample in gas phase;

Total production amount of PO=content of PO in gas phase+content of PO in liquid phase;

Selectivity to PO=total production amount of PO/amount of PO theoretically produced from propylene oxidized by CHP×100%;

The conversion rate of CHP was titrated by iodimetry and measured by a titrator.

Conversion rate of CHP=(initial value of CHP−residual amount of CHP)/initial value of CHP.

Residual amount of CHP=(titration end point−blank)×$C_{Na_2S_2O_3}$×0.001×0.5×142×total amount of liquid sample/sample amount for titration, wherein $C_{Na_2S_2O_3}$ is the concentration of sodium thiosulfate.

The silicon ester used in the examples is tetraethyl orthosilicate, and the titanium ester is tetrabutyl titanate.

When the catalyst is evaluated in the following examples and comparative examples, the process conditions for catalyzing the epoxidation of propylene to produce propylene oxide are as follows: the oxidant is cumyl hydroperoxide (CHP), and the reaction tube is a fixed-bed reactor with an inner diameter of 24 mm, the loading amount of the catalyst is 10 g; the molar ratio of propylene to CHP is 7:1, the mass space velocity is 3.5 hr$^{-1}$; the initial reaction temperature is 50° C., and the reaction temperature is gradually increased according to the CHP conversion rate (CHP conversion rate is guaranteed to be >99%).

EXAMPLES

Example 1

208 g of tetraethyl orthosilicate was dissolved in 792 g of isopropanol, then 1.67 g of formic acid was added as a hydrolysis catalyst, 10.8 g of deionized water was added dropwise, and the reaction was carried out at 50° C. for 1 h, the obtained liquid was denoted as liquid A;

8.5 g of tetrabutyl titanate was weighed and dissolved in 19.8 g of isopropanol, the obtained solution was added dropwise to liquid A, stirred evenly and the obtained liquid was denoted as liquid B; 0.067 g of NH$_4$ReO$_4$ and 0.17 g of ZnCl$_2$ were weighed and dissolved in 25.2 g of deionized water, the obtained solution was added dropwise to liquid B, stirred evenly and the obtained liquid was denoted as liquid C. The liquid C was reacted for 4 h to form a sol;

The sol was sprayed into liquid ammonia using a centrifugal atomizer for molding, a catalyst precursor was obtained;

Then, the catalyst precursor was subjected to a pore broadening treatment at 80° C. for 15 h (with liquid ammonia as the pore broadening agent).

The pore broadened catalyst precursor was dried in an oven at 80° C. for 2 h, and calcined in a muffle furnace at 550° C. for 3 h.

The calcined sample was subjected to a gas-phase silanization treatment: 3 g of hexamethyldisilazane was added to the vaporization tank, the heating temperature of the vaporization tank was 130° C., the hexamethyldisilazane vapor was brought into the reaction tube with N$_2$ to react with the calcined sample, the linear velocity of N$_2$ in the reaction tube was 1 cm/s, the silanization temperature was 200° C. and the silanization time was 180 min; the obtained catalyst was denoted as TS-A1.

Figure 1:
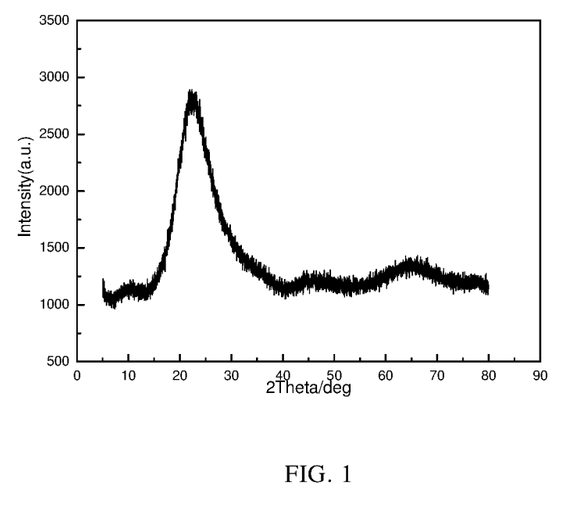
FIG. 1 is an XRD pattern of the catalyst of Example 1.

The specific surface area of the TS-A1 catalyst was 278.9 m$^2$/g, the pore volume was 0.93 ml/g, the average pore diameter was 9.7 nm, determined by the BET method; the average strength was 26.2 N/particle. XRD characterization of the TS-A1 catalyst (see FIG. 1) did not obtain any diffraction peaks of Ti species (TiO$_2$ or other Ti-containing compounds), the results can reflect a good dispersion of Ti species from one aspect. The TS-A1 was evaluated and continuously operated for 480 hours, the reaction temperature was increased from the initial 50° C. to 65° C., samples were taken for gas chromatography analysis, the CHP conversion rate was >99.9%, and the selectivity to PO was up to 96.8% with an average of 96.1%.

Example 2

249.6 g of tetraethyl orthosilicate was dissolved in 750.4 g of isopropanol, then 2.5 g of formic acid was added as a hydrolysis catalyst, 21.6 g of deionized water was added dropwise, and the reaction was carried out at 60° C. for 90 min, the obtained liquid was denoted as liquid A;

17.85 g of tetrabutyl titanate was weighed and dissolved in 26.78 g of isopropanol, the obtained solution was added dropwise to liquid A, stirred evenly and the obtained liquid was denoted as liquid B; 0.422 g of NH$_4$ReO$_4$ and 0.714 g of ZnCl$_2$ were weighed and dissolved in 21.6 g of deionized water, the obtained solution was added dropwise to liquid B, stirred evenly and the obtained liquid was denoted as liquid C. The liquid C was reacted for 2 h to form a sol;

The sol was sprayed into liquid ammonia using a centrifugal atomizer for molding, a catalyst precursor was obtained;

Then, the catalyst precursor was subjected to a pore broadening treatment at 120° C. for 6 h (with liquid ammonia as the pore broadening agent).

The pore broadened catalyst precursor was dried in an oven at 100° C. for 3 h, and calcined in a muffle furnace at 450° C. for 5 h.

The calcined sample was subjected to a gas-phase silanization treatment: 7.2 g of hexamethyldisilazane was added to the vaporization tank, the heating temperature of the vaporization tank was 140° C., the hexamethyldisilazane vapor was brought into the reaction tube with N$_2$ to react with the calcined sample, the linear velocity of N$_2$ in the reaction tube was 0.5 cm/s, the silanization temperature was 250° C. and the silanization time was 120 min; the obtained catalyst was denoted as TS-A2.

Figure 2:
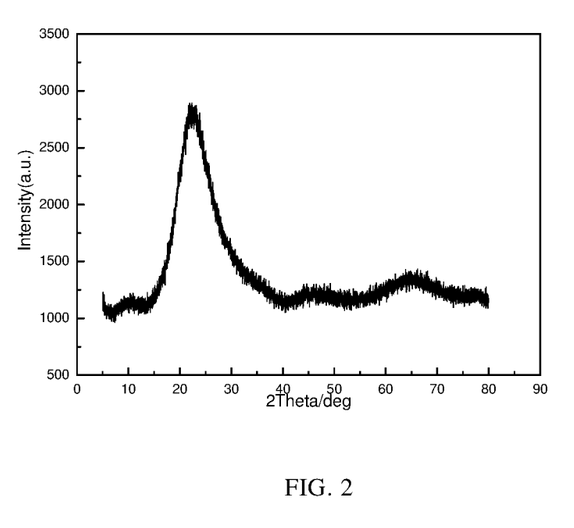
FIG. 2 is an XRD pattern of the catalyst of Example 2.

The specific surface area of the TS-A2 catalyst was 248.4 m$^2$/g, the pore volume was 1.04 ml/g, the average pore diameter was 11 nm, determined by the BET method; the average strength was 27.1 N/particle. XRD characterization of the TS-A2 catalyst (see FIG. 2) did not obtain any diffraction peaks of Ti species (TiO$_2$ or other Ti-containing compounds), the results can reflect a good dispersion of Ti species from one aspect.

The TS-A2 was evaluated and continuously operated for 1000 hours, the reaction temperature was increased from the initial 50° C. to 80° C., samples were taken for gas chromatography analysis, the CHP conversion rate was >99.9%, and the selectivity to PO was up to 97.8% with an average of 97.5%.

Example 3

291.2 g of tetraethyl orthosilicate was dissolved in 707.8 g of isopropanol, then 4.36 g of acetic acid was added as a hydrolysis catalyst, 50.4 g of deionized water was added dropwise, and the reaction was carried out at 70° C. for 140 min, the obtained liquid was denoted as liquid A;

29.75 g of tetrabutyl titanate was weighed and dissolved in 29.75 g of isopropanol, the obtained solution was added dropwise to liquid A, stirred evenly and the obtained liquid was denoted as liquid B; 1.172 g of NH$_4$ReO$_4$ and 1.785 g of ZnCl$_2$ were weighed and dissolved in 10.08 g of deionized water, the obtained solution was added dropwise to liquid B, stirred evenly and the obtained liquid was denoted as liquid C. The liquid C was reacted for 1 h to form a sol;

The sol was sprayed into liquid ammonia using a centrifugal atomizer for molding, a catalyst precursor was obtained;

Then, the catalyst precursor was subjected to a pore broadening treatment at 140° C. for 3 h (with liquid ammonia as the pore broadening agent).

The pore broadened catalyst precursor was dried in an oven at 120° C. for 5 h, and calcined in a muffle furnace at 600° C. for 2 h.

The calcined sample was subjected to a gas-phase silanization treatment: 12.6 g of hexamethyldisilazane was added to the vaporization tank, the heating temperature of the vaporization tank was 150° C., the hexamethyldisilazane vapor was brought into the reaction tube with $N_2$ to react with the calcined sample, the linear velocity of $N_2$ in the reaction tube was 0.6 cm/s, the silanization time was 100 min and the silanization temperature was 300° C.; the obtained catalyst was denoted as TS-A3.

Figure 3:
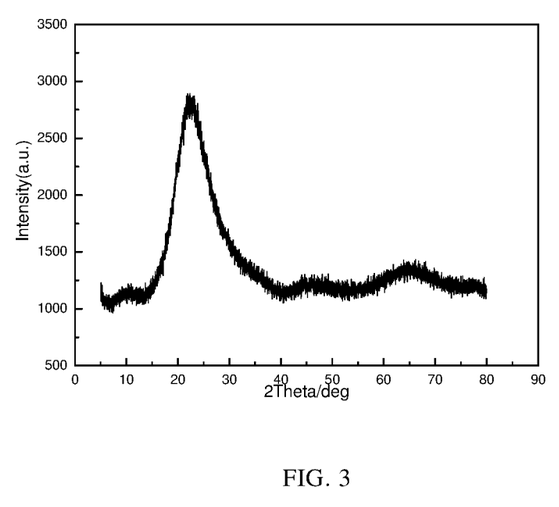
FIG. 3 is an XRD pattern of the catalyst of Example 3.

The specific surface area of the TS-A3 catalyst was 208.6 $m^2/g$, the pore volume was 1.2 ml/g, the average pore diameter was 12.8 nm, determined by the BET method; the average strength was 26.0 N/particle. XRD characterization of the TS-A3 catalyst (see FIG. 3) did not obtain any diffraction peaks of Ti species ($TiO_2$ or other Ti-containing compounds), the results can reflect a good dispersion of Ti species from one aspect.

The TS-A3 was evaluated and continuously operated for 800 hours, the reaction temperature was increased from the initial 50° C. to 90° C., samples were taken for gas chromatography analysis, the CHP conversion rate was >99.9%, and the selectivity to PO was up to 97.2% with an average of 96.9%.

Example 4

249.6 g of tetraethyl orthosilicate was dissolved in 750.4 g of isopropanol, then 2.5 g of formic acid was added as a hydrolysis catalyst, 21.6 g of deionized water was added dropwise, and the reaction was carried out at 60° C. for 90 min, the obtained liquid was denoted as liquid A;

17.85 g of tetrabutyl titanate was weighed and dissolved in 26.78 g of isopropanol, the obtained solution was added dropwise to liquid A, stirred evenly and the obtained liquid was denoted as liquid B; 21.6 g of deionized water was added dropwise to liquid B. The liquid B was reacted for 3 h to form a sol;

The sol was sprayed into liquid ammonia using a centrifugal atomizer for molding, a catalyst precursor was obtained;

Then, the catalyst precursor was subjected to a pore broadening treatment at 120° C. for 6 h (with liquid ammonia as the pore broadening agent).

The pore broadened catalyst precursor was dried in an oven at 100° C. for 3 h, and calcined in a muffle furnace at 450° C. for 5 h.

The calcined sample was subjected to a gas-phase silanization treatment: 7.2 g of hexamethyldisilazane was added to the vaporization tank, the heating temperature of the vaporization tank was 140° C., the hexamethyldisilazane vapor was brought into the reaction tube with $N_2$ to react with the calcined sample, the linear velocity of $N_2$ in the reaction tube was 0.5 cm/s, the silanization temperature was 250° C. and the silanization time was 120 min; the obtained catalyst was denoted as TS-A4.

Figure 4:
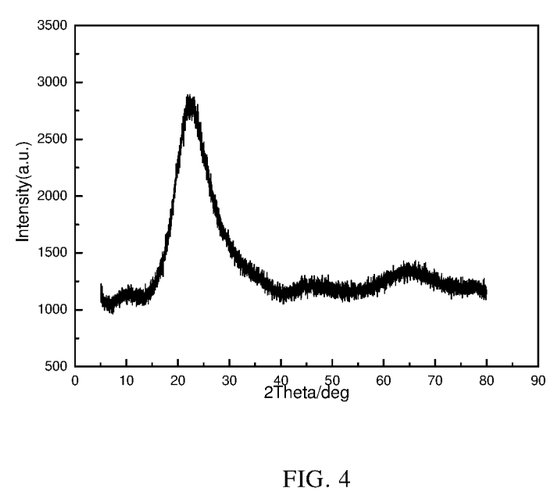
FIG. 4 is an XRD pattern of the catalyst of Example 4.

The specific surface area of the TS-A4 catalyst was 248.2 $m^2/g$, the pore volume was 1.04 ml/g, the average pore diameter was 11 nm, determined by the BET method; the average strength was 26.6 N/particle. XRD characterization of the TS-A4 catalyst (see FIG. 4) did not obtain any diffraction peaks of Ti species ($TiO_2$ or other Ti-containing compounds), the results can reflect a good dispersion of Ti species from one aspect.

The TS-A4 was evaluated and continuously operated for 600 hours, the reaction temperature was increased from the initial 60° C. to 90° C., samples were taken for gas chromatography analysis, the CHP conversion rate was >99.9%, and the selectivity to PO was up to 93.8% with an average of 92.7%.

Comparative Example 1

249.6 g of tetraethyl orthosilicate was dissolved in 750.4 g of isopropanol, then 2.5 g of formic acid was added as a hydrolysis catalyst, 21.6 g of deionized water was added dropwise, and the reaction was carried out at 60° C. for 90 min, the obtained liquid was denoted as liquid A;

17.85 g of tetrabutyl titanate was weighed and dissolved in 26.78 g of isopropanol, the obtained solution was added dropwise to liquid A, stirred evenly and the obtained liquid was denoted as liquid B; 21.6 g of deionized water was added dropwise to liquid B, stirred evenly and the obtained liquid was denoted as liquid C. The liquid C was reacted for 1 h to form a sol;

The sol was aged for 12 h to form a gel.

The gel was then dried in an oven at 100° C. for 3 h, crushed, sieved for particles of 0.4-1.2 mm, and calcined in a muffle furnace at 450° C. for 5 h.

The calcined sample was subjected to a gas-phase silanization treatment: 7.2 g of hexamethyldisilazane was added to the vaporization tank, the heating temperature of the vaporization tank was 140° C., the hexamethyldisilazane vapor was brought into the reaction tube with $N_2$ to react with the calcined sample, the linear velocity of $N_2$ in the reaction tube was 0.5 cm/s, the silanization temperature was 250° C. and the silanization time was 120 min; the obtained catalyst was denoted as TS-A5.

The specific surface area of the TS-A5 catalyst was 17.6 $m^2/g$, the pore volume was 12.3 ml/g, the average pore diameter was 1.2 nm, determined by the BET method; the average strength of a single particle was 14.2 N/particle.

The TS-A5 was evaluated and continuously operated for 10 hours, the reaction temperature was 80° C., samples were taken for gas chromatography analysis, the CHP conversion rate was >99.9%, and the selectivity to PO was 7.4%.

Comparative Example 2

Refer to patent CN1894030 for catalyst preparation:

30 g of silica gel carrier was weighed and loaded into a reaction tube, dried under $N_2$ atmosphere at 240° C. for 240 min, and the linear velocity of $N_2$ in the reaction tube was 2 cm/s; 4.17 g of $TiCl_4$ was added to the $TiCl_4$ vaporization tank, which was heated at a temperature of 145° C., the $TiCl_4$ vapor was brought into the reaction tube with $N_2$ to react with the silica gel, the linear velocity of $N_2$ in the reaction tube was 0.8 cm/s and the deposition time was 200 min; the temperature was raised to 600° C. at a heating rate of 2° C./min, the linear velocity of $N_2$ in the reaction tube was 2 cm/s, and calcined for 200 min; 33.5 g of distilled water was added to the water and silanization reagent vaporization tank, which was heated at a temperature of 160° C., the water vapor was brought into the reaction tube with $N_2$ for washing, the linear velocity of $N_2$ in the reaction tube was 2 cm/s, and the washing time was 200 min; 2.4 g of hexamethyldisilazane was added to the water and silanization reagent vaporization tank, which was heated at a temperature of 140° C., the hexamethyldisilazane vapor was brought into the reaction tube with $N_2$ to react with the silica gel, the linear velocity of $N_2$ in the reaction tube was 0.5 cm/s, the silanization temperature was 250° C., and the silanization time was 120 min; the obtained catalyst was denoted as TS-A6.

Figure 5:
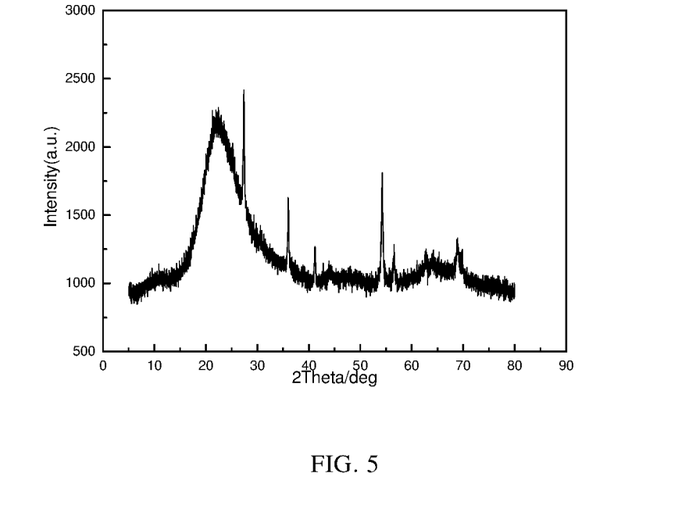
FIG. 5 is an XRD pattern of the catalyst of Comparative Example 2.

X-ray characterization of the TS-A6 catalyst (see FIG. 5) obtained the diffraction peaks of $TiO_2$ (sharp diffraction peaks in FIG. 5), indicating that the Ti—$SiO_2$ catalyst prepared by the vapor deposition method has poor dispersion of Ti species, the Ti species thereof are easy to aggregate and free titanium dioxide was produced. The TS-A6 was evaluated and continuously operated for 200 hours, the reaction temperature was increased from the initial 50° C. to 90° C., samples were taken for gas chromatography analysis, the CHP conversion rate was >99.9%, and the selectivity to PO was up to 92.8% with an average of 91.7%.

The invention claimed is:

1. A preparation method for a propylene epoxidation catalyst, comprising the following steps:
   (1) pre-hydrolysis of silicon source: dissolving a silicon ester in a lower alcohol, adding a hydrolysis catalyst and water to react to obtain liquid A;
   (2) sol formation: dissolving a titanium ester in a lower alcohol and adding the obtained system to liquid A; adding water or adding a mixed aqueous solution of $NH_4ReO_4$ and a zinc salt to react to obtain a sol;
   (3) atomizing the sol obtained in step (2) and spraying the atomized sol into liquid ammonia to obtain a catalyst precursor;
   (4) carrying out a pore broadening treatment to the catalyst precursor obtained in step (3);
   (5) drying and calcining the pore broadened catalyst precursor in step (4);
   (6) carrying out a silanization treatment to the product obtained in step (5).

2. The method according to claim 1, wherein the silicon ester in step (1) is selected from the group consisting of tetraethyl orthosilicate, tetramethyl orthosilicate, tetrapropyl orthosilicate and tetrabutyl orthosilicate and combinations thereof.

3. The method according to claim 1, wherein the hydrolysis catalyst in step (1) is one of acetic acid and formic acid or a mixture thereof.

4. The method according to claim 3, wherein, in step (1), the hydrolysis catalyst is added in an amount that is 0.8-1.5 wt % of the silicon ester; water is added in an amount that is the amount of water theoretically required to hydrolyze 30-80 wt % of the silicon ester;
   the reaction temperature in step (1) is 40-70° C., and the reaction time is 1-3 h.

5. The method according to claim 1, wherein the titanium ester used in step (2) is selected from the group consisting of tetramethyl titanate, tetraethyl titanate, tetrapropyl titanate, tetraisopropyl titanate, tetrabutyl titanate and tetraisobutyl titanate and combinations thereof.

6. The method according to claim 5, wherein, based on the weight of $SiO_2$ corresponding to $SiO_2$ from the complete hydrolysis of the raw silicon ester in step (1), the amount of Ti in the titanium ester used in step (2) is 2-5% of the weight of $SiO_2$;
   in step (2), the concentration of the titanium ester in the lower alcohol is 30-50 wt %;
   the reaction time in step (2) is 1~4 h.

7. The method according claim 1, wherein in step (2), the molar ratio of Re in the used $NH_4ReO_4$ to Ti in the used titanium ester is 0.01-0.05:1, and the molar ratio of Zn in the used zinc salt to Ti in the used titanium ester is 0.05-0.15:1.

8. The method according to claim 7, wherein in step (2), if water is added for the reaction to form a sol, water is added in an amount that is the amount of water required for theoretical complete hydrolysis of the unhydrolyzed silicone ester in step (1) and the titanium ester in step (2);
   in step (2), if the mixed aqueous solution of $NH_4ReO_4$ and a zinc salt is added for the reaction to form a sol, the amount of water contained in the mixed aqueous solution of $NH_4ReO_4$ and a zinc salt is the amount of water required for theoretical complete hydrolysis of the unhydrolyzed silicone ester in step (1) and the titanium ester in step (2).

9. The method according to claim 7, wherein a pore broadening agent used in step (4) for performing the pore broadening treatment is liquid ammonia.

10. The method according to claim 9, wherein the process conditions for the pore broadening treatment in step (4) include: the pore broadening temperature is 60-140° C., and the pore broadening time is 3-15 h.

11. The method according to claim 1, wherein in step (2), if water is added for the reaction to form a sol, water is added in an amount that is the amount of water required for theoretical complete hydrolysis of the unhydrolyzed silicone ester in step (1) and the titanium ester in step (2);
   in step (2), if the mixed aqueous solution of $NH_4ReO_4$ and a zinc salt is added for the reaction to form a sol, the amount of water contained in the mixed aqueous solution of $NH_4ReO_4$ and a zinc salt is the amount of water required for theoretical complete hydrolysis of the unhydrolyzed silicone ester in step (1) and the titanium ester in step (2).

12. The method according to claim 11, wherein a pore broadening agent used in step (4) for performing the pore broadening treatment is liquid ammonia.

13. The method according to claim 12, wherein the process conditions for the pore broadening treatment in step (4) include: the pore broadening temperature is 60-140° C., and the pore broadening time is 3-15 h.

14. The method according to claim 1, wherein an atomizer is used in the step (3) to atomize the sol, and the sol sprayed by the atomizer has an average particle diameter that is from 100 to 850 μm.

15. The method according to claim 14, wherein the sol sprayed by the atomizer has an average particle diameter that is from 400 to 580 μm.

16. The method according to claim 1, wherein a pore broadening agent used in step (4) for performing the pore broadening treatment is liquid ammonia.

17. The method according to claim 16, wherein the process conditions for the pore broadening treatment in step (4) include: the pore broadening temperature is 60-140° C., and the pore broadening time is 3-15 h.

18. The method according to claim 1, wherein in the step (5), the drying temperature is 80-120° C.; the calcination temperature is 450-600° C.

19. The method according to claim 1, wherein a silanization agent used in the silanization treatment in step (6) is hexamethyldisilazane; based on the weight of $SiO_2$ corresponding to the $SiO_2$ from complete hydrolysis of the raw silicon ester in step (1), the amount of the hexamethyldisilazane used is 5-15 wt %.

20. The method according to claim 19, wherein the temperature of hexamethyldisilazane used for the silanization treatment is 126-150° C., the temperature of the silanization treatment is 200-300° C., and the time of the silanization treatment is 60-180 min.

21. The method according to claim 1, wherein the lower alcohol in step (1) and step (2) is selected from C1-C3 alcohols.

22. A method for preparing propylene oxide, comprising contacting under epoxidation conditions a feedstock with the catalyst prepared by the method according to claim 1 to produce a product comprising said propylene oxide.

\* \* \* \* \*